(12) United States Patent
King et al.

(10) Patent No.: US 12,102,336 B2
(45) Date of Patent: Oct. 1, 2024

(54) CRIMP ATTACHMENT OF CLIP FOR RELOADABLE HEMOSTASIS DEVICE

(71) Applicant: BOSTON SCIENTIFIC SCIMED, INC., Maple Grove, MN (US)

(72) Inventors: Joseph W. King, Franklin, MA (US); Laurie A. Lehtinen, Boylston, MA (US); Henry Stock, Sanbornton, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/517,928

(22) Filed: Nov. 22, 2023

(65) Prior Publication Data
US 2024/0081831 A1    Mar. 14, 2024

Related U.S. Application Data

(63) Continuation of application No. 16/905,616, filed on Jun. 18, 2020, now Pat. No. 11,883,036.

(60) Provisional application No. 62/874,695, filed on Jul. 16, 2019.

(51) Int. Cl.
A61B 17/128    (2006.01)
A61B 17/122    (2006.01)
A61B 17/00     (2006.01)

(52) U.S. Cl.
CPC ........ *A61B 17/1285* (2013.01); *A61B 17/122* (2013.01); *A61B 2017/0034* (2013.01); *A61B 2017/00818* (2013.01)

(58) Field of Classification Search
CPC . A61B 17/122; A61B 17/1222; A61B 17/128; A61B 17/1285; A61B 2017/0034; A61B 2017/00477
See application file for complete search history.

(56) References Cited

U.S. PATENT DOCUMENTS

2017/0104475 A1    4/2017 Lam
2020/0205836 A1*   7/2020 Uesaka .............. A61B 17/1285

FOREIGN PATENT DOCUMENTS

CN    102274061 A    12/2011
CN    103584898 A    2/2014

* cited by examiner

*Primary Examiner* — Brooke Labranche
(74) *Attorney, Agent, or Firm* — Fay Kaplun & Marcin, LLP

(57) ABSTRACT

A system includes a clip having a pair of clip arms, proximal ends of the clip arms received within a channel of a capsule to be moved between an open configuration and a closed configuration. A proximal end of the capsule including a plurality of connecting elements extending proximally therefrom. Each of the connecting elements including a hook along a proximal portion thereof. An applicator includes an elongated flexible member and a control member extending therethrough, the control member configured to be connected to the clip arms to move the clip assembly between the open and closed configurations, the elongated flexible member including a bushing including a first ramped portion and a necked portion extending proximally from the first ramped portion, a proximal end of the first ramped portion including a lip configured to engage the hook when the connecting elements are crimped thereover.

13 Claims, 4 Drawing Sheets

CRIMP ATTACHMENT OF CLIP FOR RELOADABLE HEMOSTASIS DEVICE

PRIORITY CLAIM

The present application is a Continuation of U.S. patent application Ser. No. 16/905,616 filed on Jun. 18, 2020; which claims priority to U.S. Provisional Patent Application Ser. No. 62/874,695 filed Jul. 16, 2019. The disclosures of the above application(s)/patent(s) are incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be used.

SUMMARY

The present disclosure relates to a reloadable clipping system for treating tissue, comprising a clip including a pair of clip arms, each of the clip arms extending from a proximal end to a distal end, proximal ends of the clip arms slidably received within a channel of a capsule to be moved between an open configuration and a closed configuration. A proximal end of the capsule includes a plurality of connecting elements extending proximally therefrom, each of the connecting elements including a hook along a proximal portion thereof. An applicator includes an elongated flexible member and a control member extending therethrough. The control member includes a distal end configured to be connected to the clip arms to move the clip assembly between the open configuration and the closed configuration. A distal end of the elongated flexible member includes a bushing including a first ramped portion tapering to a distal end of the bushing and a necked portion extending proximally from the first ramped portion. A proximal end of the first ramped portion includes a lip defined via a recess extending between an interior surface of the first ramped portion and an exterior surface of the necked portion, the lip configured to engage the hook when the connecting elements are crimped thereover.

In one embodiment, the bushing may include a second ramped surface flaring proximally outward from a proximal end of the necked portion.

In one embodiment, the connecting elements may be formed of a metal material configured to permit an elastic deformation thereof during a loading of the clip when the connecting elements are slid proximally along an exterior surface of the first ramped portion and a plastic deformation of the connecting elements when a compressive force exerted on the connecting elements exceeds a predetermined threshold value so that connecting elements slide proximally along the second ramped portion of the bushing toward a deployed configuration in which the bushing is releasable from therebetween.

In one embodiment, the reloadable clipping system may further comprise a cartridge including a space sized and shaped to house the clip therein, in the open configuration, and a longitudinal slot extending proximally from the space, the longitudinal slot sized and shaped to receive a distal portion of the applicator therein.

In one embodiment, the longitudinal slot may include a crimping feature configured to engage the distal portion of the connecting elements when the connecting elements are moved proximally therepast so that the hook of the connecting elements crimp the hook over the lip of the first ramped portion.

In one embodiment, the crimping feature may include a ramped surface tapering toward a distal end so that the ramped surface exerts a radially inward and a distal force to the hook so that a tip of the hook is received within the cavity defining the lip.

In one embodiment, the longitudinal slot may include a stop along a portion thereof configured to engage a portion of the bushing to prevent the bushing from moving distally therebeyond.

In one embodiment, the first and second ramped portions may define substantially conically shaped portions of the bushing while the neck portion extends along a cylindrical portion of the bushing.

In one embodiment, the hook may extend along a substantially J-shape so that a tip of the hook extends toward a distal direction.

The present disclosure relates to a reloadable a clip device, comprising a clip including a pair of clip arms, each of the clip arms extending from a proximal end to a distal end, proximal ends of the clip arms slidably received within a channel of a capsule to be moved between an open configuration and a closed configuration. A proximal end of the capsule includes a plurality of connecting elements extending proximally therefrom, each of the connecting elements including a hook along a proximal portion thereof. A cartridge includes a space sized and shaped to house the clip therein, in the open configuration, and a longitudinal slot extending proximally from the space, the longitudinal slot sized and shaped to receive a distal portion of an applicator to be coupled to the clip therein.

In one embodiment, the connecting elements may be formed of a metal material configured to permit an elastic deformation thereof during a coupling of the capsule to a portion of the applicator and a plastic deformation thereof when a force exerted thereon exceeds a predetermined threshold value.

In an embodiment, the longitudinal slot may include a crimping feature configured to engage the distal portion of the connecting elements when the connecting elements are moved proximally therepast so that the hook of the connecting elements crimp the hook over a corresponding portion of the applicator receivable therebetween.

In an embodiment, the crimping feature may include a ramped surface tapering toward a distal end so that the ramped surface exerts both a radially inward and a distal force to the hook.

In one embodiment, the longitudinal slot may include a stop along a portion thereof configured to engage a portion of the applicator receivable therein.

In one embodiment, the hook may extend along a substantially J-shape so that a tip of the hook extends toward a distal direction.

The present disclosure also relates to a method for loading a clip onto an applicator for a reloadable clipping system. A distal portion of an applicator is inserted through a longitudinal slot of a cartridge in which a clip is stored, the longitudinal slot extending proximally of a space within the cartridge that is sized and shaped to house the clip in the open configuration. A control member of the applicator is moved distally relative to the cartridge until an enlarged distal end of the control member is coupled to a proximal ends of clip arms of the clip. A capsule of the clip is moved proximally relative to the capsule via the control member so that connecting elements extending proximally from a proximal end of the capsule slide along an exterior surface of a first ramped portion of a bushing of the applicator until a hook at a proximal end of each of the connecting elements is moved distally beyond a proximal end of the first ramped portion, snapping thereover to form a preliminary engagement. The applicator is drawn proximally relative to the cartridge so that the connecting elements of the capsule, which is preliminarily engaged to the bushing, is moved proximally a crimping feature along the longitudinal slot of the cartridge, the crimping feature engaging the hook to crimp the hook over a lip at the proximal end of the first ramped portion.

In an embodiment, the distal portion of the applicator is inserted through the longitudinal slot until a portion of the bushing engages a stop extending along a portion of the longitudinal slot.

In an embodiment, the crimping feature is configured as a ramped surface angled so that when the connecting elements are moved proximally therealong, the ramped surface exerts both a distal and radially inward force on the hook to crimp the hook over the lip.

In one embodiment, the lip is defined via a cavity extending between an interior surface of the first ramped portion and an exterior surface of a neck portion extending proximally from the first ramped portion, a tip of the hook received within the cavity when the hook is crimped over the lip.

In one embodiment, the bushing of the applicator includes a second ramped portion flaring proximally outward from a proximal end of the neck portion.

BRIEF DESCRIPTION

DETAILED DESCRIPTION

Figure 1:
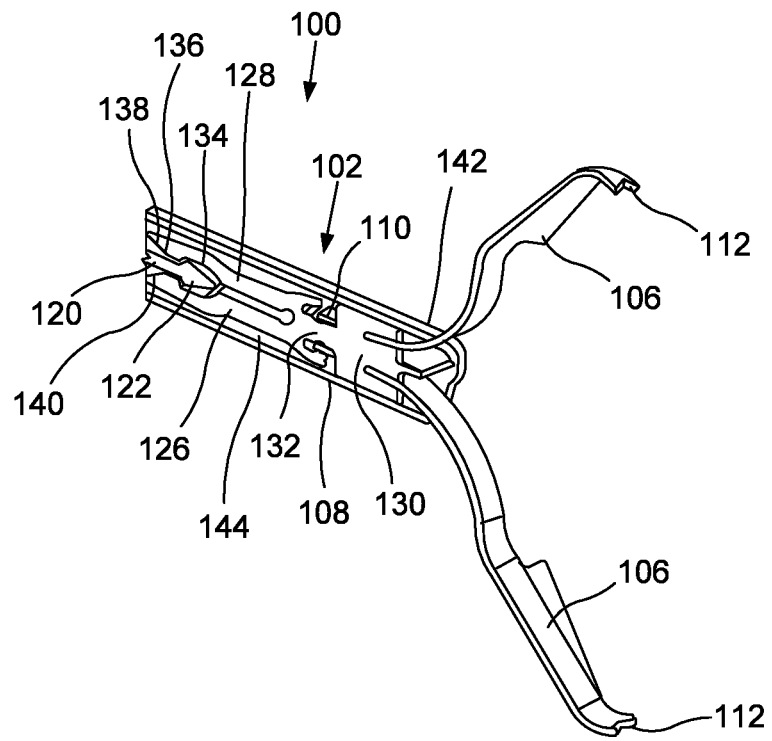
FIG. 1 shows a cross-sectional perspective view of a portion of a reloadable clipping system according to an exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system, in which a clip may be loaded onto a distal end of an applicator prior to an endoscopic procedure. Once a clip has been deployed at a desired target area in the body, the applicator may be reloaded with a new clip. Although shed parts (e.g., parts that are left in a body upon deployment of the clip) generally pass naturally from the body, shed parts may become trapped in larger defects after closure.

Exemplary embodiments of the present disclosure comprise a clip including clip arms slidable within a capsule to move between an open configuration and a closed configuration to clip tissue, as desired. A proximal end of the capsule includes a pair of connecting elements extending proximally therefrom and configured to be crimped over a portion of the applicator via a crimping feature in a cartridge, which holds and stores the clip prior to loading of the clip onto the applicator. The crimped connection between the clip and the applicator facilitates a direct releasable connection with the applicator, which minimizes or eliminates the potential for shed parts upon deployment of the clip. It will be understood by those of skill in the art that the terms proximal and distal as used herein, are intended to refer to a direction toward and away from, respectively, a user of the device.

As shown in FIGS. 1-9, a reloadable clipping system 100 comprises a clip 102 configured to be loaded onto an applicator 104 prior to insertion of the system 100 into a body to clip target tissue therein. The clip 102 includes a pair of clip arms 106, proximal ends 110 of which are slidably received within a capsule 108 so that the clip arms 106 may move between an open configuration, in which distal ends 112 of the clip arms 104 are separated from one another, and a closed configuration, in which distal ends 112 are drawn toward one another to grip tissue. A proximal end 114 of the capsule 108 includes a pair of connecting elements 116 extending proximally therefrom and configured to be crimped over, for example, a bushing 118 of the applicator 104 during a loading of the clip 102 onto the applicator 104.

Prior to loading of the clip 102 into the applicator 104, the clip 102 is stored in a cartridge 124 including a crimping feature 146 so that when a distal portion of the applicator 104 is inserted into the cartridge 124, the capsule 108 may be drawn proximally over the bushing 118 until the crimping feature 146 of the applicator 104 engages the connecting elements 116 to crimp the connecting elements 116 over a portion of the bushing 118. During loading of the clip 102, an enlarged distal end 122 of a control member 120 of the applicator 104 is also coupled to the clip arms 106 so that longitudinal movement of the control member 120 relative to the capsule 108 moves the clip 102 between the open and closed configurations.

As will be described in further detail below, once the target tissue has been clipped, as desired, a user (e.g., physician) of the system 100 initiates a deployment process in which a compressive load is exerted on the connecting elements 116, causing the connecting elements 116 to move away from a centerline of the capsule 108, toward a deployed configuration, so that the bushing 118 is released therefrom. In the deployed configuration, the connecting elements 116 are plastically deformed without fracture to release the bushing 118 therefrom so that deployment of the clip 102 does not leave any shed parts in the body. The applicator 104 is configured so that, after deployment of the clip 102, a new clip 102 may be loaded onto the applicator 104 so that the same applicator 104 may be used to deliver the new clip 102 to a second portion of target tissue in the body. Each clip 102 according to this embodiment is stored in a cartridge 124, which facilitates loading of the clip assembly 102 onto the applicator 104.

As shown in FIG. 1, the clip 102 includes the pair of clip arms 106, proximal ends 110 of which are, in this embodiment, connected to one another via a yoke 126 slidably received within the capsule 108. In this embodiment, the clip arms 106 are biased toward the open configuration so that, when not constrained by the capsule 108, the clip arms 106 move under their natural bias to the open configuration in which the distal ends 112 of the clip arms 106 spread apart from one another to receive tissue therebetween. When the clip arms 106 are drawn into the capsule 108, the capsule 108 constrains the clip arms 106, holding the distal ends 112 together so that tissue may be gripped therebetween. The yoke 126 is longitudinally slidable within the capsule 108 to move the clip arms 106 proximally and distally relative to the capsule 108 between the open and closed configurations.

Each of the clip arms 106 extends from the proximal end 110, connected to the yoke 126, to the distal end 112. The distal ends 112 of one or both of the clip arms 106 may include tips extending laterally inward toward the other clip arm 106 with the tips including, for example, teeth, protrusions, spikes or other structures configured to grip tissue between the distal ends 112. One or both of the clip arms 106 may also include a locking feature configured to lock the clip arms 106 in the tissue gripping configuration after target tissue has been gripped as desired by the clip arms 106. In one embodiment, one or both of the clip arms 106 includes a locking tab extending laterally outward therefrom configured to engage a portion of the capsule 108 when the clip arms 106 have been drawn into the capsule 108 by a predetermined distance. For example, the locking tabs may be received within correspondingly sized, shaped and positioned locking windows extending laterally into or through a wall of the capsule 108 to lock the clip arms 106 relative to the capsule 108, in the tissue gripping configuration.

The yoke 126 is connected to the proximal ends 110 of the clip arms 106 and is configured to be connected to the enlarged distal end 122 of the control member 120. In this embodiment, the yoke 126 includes a proximal portion 128 and a distal portion 130 connected to one another at a point 132 configured to break or separate when subject to a force exceeding a predetermined threshold value. For example, the point 132 may include a welding, a decreased diameter portion, or an adhesive that breaks or otherwise uncouples when sufficient force is exerted thereon. The distal portion 130 is configured to engage proximal portions of the clip arms 106 via, for example, a pair of protrusions extending therefrom and received within correspondingly sized and shaped openings extending through proximal portions of the clip arms 106 so that the clip arms 106 are held in position relative to one another.

The proximal portion 128 is configured to engage the enlarged distal end 122 of the control member 120. In one embodiment, the proximal portion 128 includes a cavity 134 sized and shaped to receive the enlarged distal end 122 and a longitudinal slot 136 extending proximally from the cavity 134 to a proximal end 138 of the yoke 126. The longitudinal slot 136 is sized and shaped to receive a portion of the control member 120 extending proximally from the enlarged distal end 122. In one embodiment, an opening of the longitudinal slot 136 at the proximal end 138 includes an angled surface 140 tapering toward a distal end thereof to facilitate insertion of the enlarged distal end 122 distally through the longitudinal slot 136 and into the cavity 134 during loading the clip 102 onto the applicator 104. The cavity 134 and the longitudinal slot 136 are configured so that, once the enlarged distal end 122 has been forced through the slot 136 into the cavity 134, the slot 136 retracts in diameter to prevent the enlarged distal end 122 from being proximally withdrawn therefrom. Thus, longitudinal movement of the control member 120 relative to the capsule 108 moves the clip arms 106 between the open and the closed configurations.

The capsule 108 extends longitudinally from the proximal end 114 to a distal end 142 and includes a channel 144 extending longitudinally therethrough. The channel 144 is sized and shaped to slidably receive the yoke 126 and the clip arms 106 therein. As described above, the capsule 108 of this embodiment also includes locking structures (e.g., locking windows) for engaging corresponding locking features (e.g., locking tabs) of the clip arms 106. The capsule 108 includes the connecting elements 116 which, in an initial configuration, extend proximally from the proximal end 114 so that the connecting elements 116 are substantially diametrically opposed to one another. Although the capsule 108 is shown and described as including two connecting elements 116, it will be understood by those of skill in the art that the capsule 108 may include more than two connecting elements and, according to another embodiment, for example, may include four connecting elements 116 extending proximally from the proximal end 114 about a periphery thereof.

As would be understood by those skilled in the art, these connecting elements 116 may be distributed around a circumference of the capsule 108 in any desired pattern but are generally equally dispersed therearound. A distal portion 148 of each of the connecting elements 116 extends at an angle relative to the longitudinal axis of the capsule 108 away from the longitudinal axis of the capsule 108—flaring away from a longitudinal axis of the capsule 108. A proximal portion 150 of each of the connecting elements 116 includes a hook 152 configured to engage a corresponding portion of the bushing 118. As will be described in further detail below, the proximal portion 150 is crimped over the bushing 118 so that the hook 152 engages the corresponding portion of the bushing 118. In one embodiment, the proximal portion of the hook 152 extends along a substantially J-shaped curve so that a tip 154 of the hook 152 extends toward a distal direction.

Figure 2:
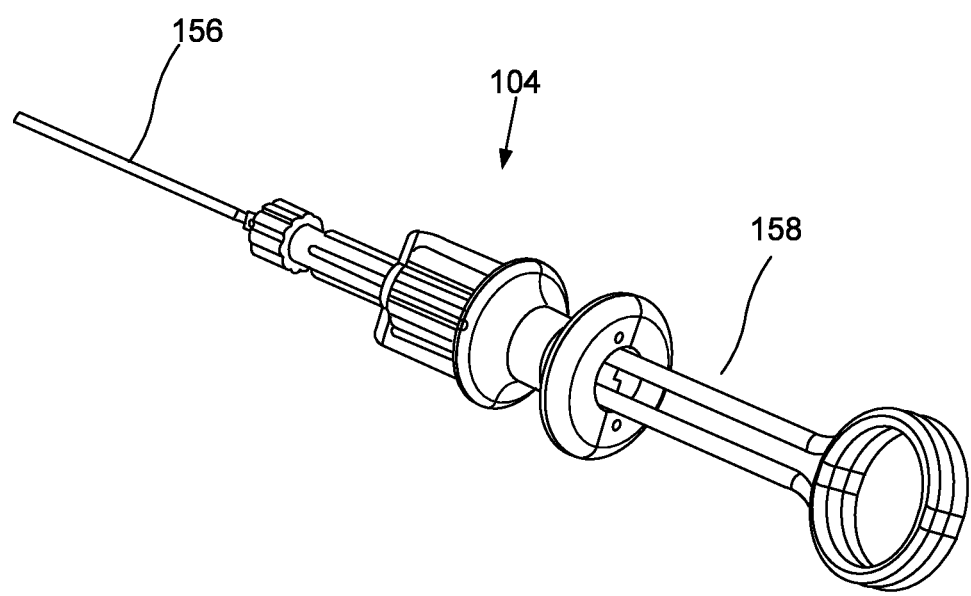
FIG. 2 shows a perspective view of an applicator according to the system of FIG. 1.

As shown in FIG. 2, the applicator 104 includes a flexible member 156 such as, for example, a catheter extending from a proximal end connected to a handle portion 158 that remains outside of the body during the clipping of target tissue, to a distal end including, for example, the bushing 118 for connecting the applicator 104 to the clip 102. The control member 120 extends through the flexible member 156 from a proximal end connected to the handle portion 158, which includes actuators for controlling a movement of the clip 102 once the clip 102 has been loaded onto the applicator 104, to the enlarged distal end 122.

In this embodiment, the bushing 118 is connected to the distal end of the flexible member 156 and is configured to be connected to the clip 102 via the connecting elements 116 of the capsule 108. The bushing 118 extends from a proximal end 160 to a distal end 162 and includes a channel 164 extending therethrough. The proximal end 160 is connected to the distal end of the flexible member 154 while the distal end 162 is configured to engage the connecting elements 116. When the bushing 118 is coupled to the capsule 108, the channel 164 of the bushing 118 is substantially aligned with the channel 144 of the capsule 108. The bushing includes a first ramped portion 166 configured to engage the connecting elements 116 during loading of the clip 102 onto the applicator 104 and a second ramped portion 168 facilitating separation of the capsule 108 from the bushing 118 during a deployment of the clip 102. The first and second ramped portions 166, 168 are, in this embodiment, connected to one another via a neck portion 170. The first and second ramped portions 166, 168 extend about a periphery of the bushing 118 and, in one embodiment, form substantially conical portions of the bushing 118. The neck portion 170 similarly extends about a periphery of the bushing 118, proximally from the first ramped portion 166 to a distal end of the second ramped portion 168, along a substantially cylindrical portion of the bushing 118.

An exterior surface 172 of the first ramped portion 166 tapers to the distal end 162 to facilitate receipt of the bushing 118 between the connecting elements 116. The first ramped portion 166 includes a lip 174 at a proximal end thereof, the lip 174 defined by a space formed between an interior surface of the first ramped portion 166 and an exterior surface 176 of the neck portion 170. A portion of the first ramped portion 166 forming the lip 174 has a larger diameter than the distal end 162 such that, as the capsule 108 is drawn proximally relative to the bushing 118 during loading of the clip 102, the hook 152 slides along the exterior surface 172 of the first ramped portion 166 so that the connecting elements 116 elastically deform to accommodate the first ramped portion 166 therebetween. Once the hook 152 has moved proximally past the lip 174, the connecting elements 116 snap radially inward reverting to their initial configuration.

In this configuration, the hook 152 and the first ramped portion 166 form a preliminary engagement in which the tip 154 of the hook 152 abuts an edge 176 of the lip 174. As will be described in further detail below, once the capsule 108 and the bushing 118 have formed this preliminary engagement, drawing the applicator 104 and the clip 102 out of the cartridge 124 engages the crimping feature 146 of the cartridge 124 with the proximal portion 150 of the connecting elements 116 so that the hook 152 is crimped over the lip 174 of the first ramped portion 166, loading the clip 102 onto the applicator 104. After the hook 152 has been crimped over the lip 174, the clip 102 remains coupled to the bushing 118 of the applicator 104 until deployment.

The second ramped portion 168 extends proximally from neck portion 170, flaring outward therefrom so that a proximal end 178 of the second ramped portion 168 has a larger diameter than both the neck portion 170 and portion of the first ramped portion 166 including the lip 174. Once the clip 102 has been clipped over target tissue as desired, the control member 120 is drawn proximally with respect to the capsule 108 until the clip arms 106 are locked relative to the capsule 108 (e.g., via locking tabs of the clip arms 106 received within locking windows of the capsule 108) in the closed configuration. Further proximal movement of the control member 120 after this point draws the capsule 108 proximally against the bushing 118 so that, when a sufficient compressive force is applied to the connecting elements 116, the hook 152 slides proximally along the second ramped portion 166, moving the connecting elements 116 toward the deployed configuration, in a direction away from the longitudinal axis of the capsule 108. The connecting elements 116 are plastically deformed toward the deployed configuration out of engagement with the bushing 118 so that the bushing 118 may be proximally removed from between the connecting elements 116 of the capsule 108 without leaving any shed parts in the body.

In one embodiment, the connecting tabs 116 are formed of a metal selected to permit the slight elastic deformation required to achieve the preliminary engagement of the connecting elements 116 with the first ramped portion 166 and which will plastically deform during deployment of the clip 102. The connecting elements 116 may be formed of a metal such as, for example, stainless steel which may be annealed or work hardened (by stamping, drawing, extruding, etc.) so that, when crimped over the bushing 118, will bear the load of the clip 102 moving between the open and the closed configurations without any deformations. Once a sufficient compressive force has been applied to the connecting elements 116, however, the connecting tabs 116 will plastically deform toward the deployed configuration.

Figure 3:
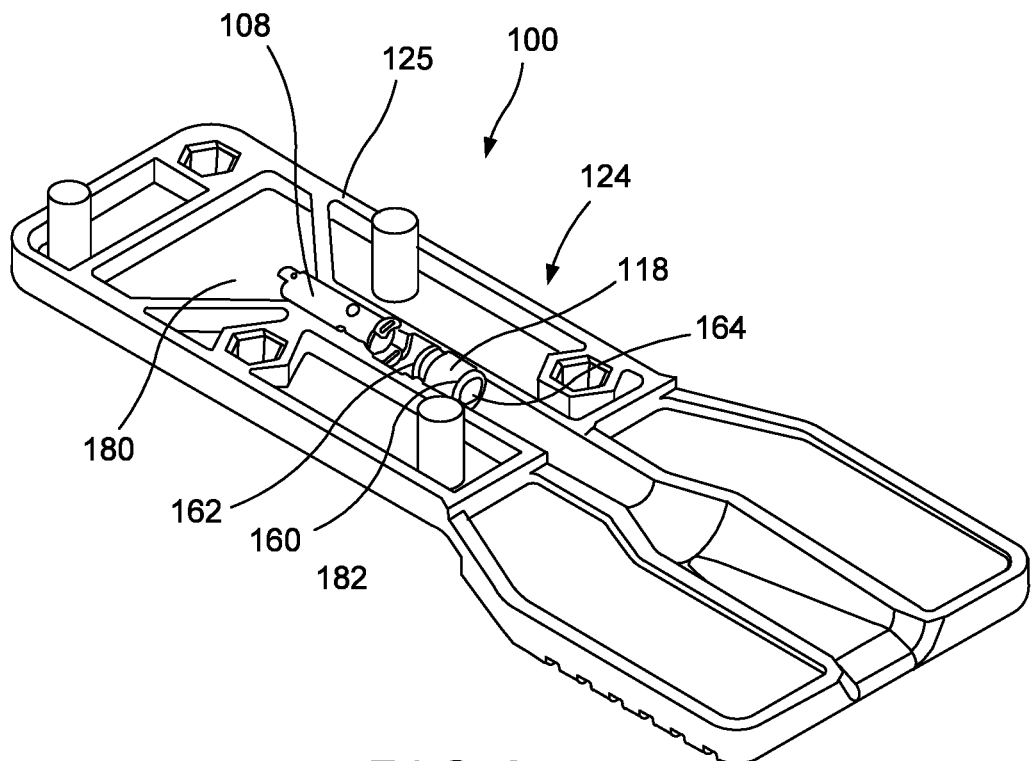
FIG. 3 shows a perspective view of a portion of a cartridge for storing a clip according to the system of FIG. 1.

Prior to being loaded on the applicator 104, the clip 102 of this embodiment is stored in the cartridge 124, which is configured to facilitate loading of the clip assembly 102 on the applicator 104. The cartridge 124, as shown in FIG. 3, is configured as a storage container including a base 125 and lid (not shown), within which a space 180 sized and shaped to house the clip 102 is defined. It should be noted that although FIG. 3 shows only the base 125 of the container 124, a corresponding lid is coupled to the base 125 to completely enclose the clip 102. In this embodiment, the clip 102 is stored within the cartridge 124 in the open configuration. Extending proximally from the space 180 is a longitudinal slot 182 through which the distal portion of the applicator 104 is inserted to be coupled to the clip assembly 102, as will be described in further detail below.

Figure 4:
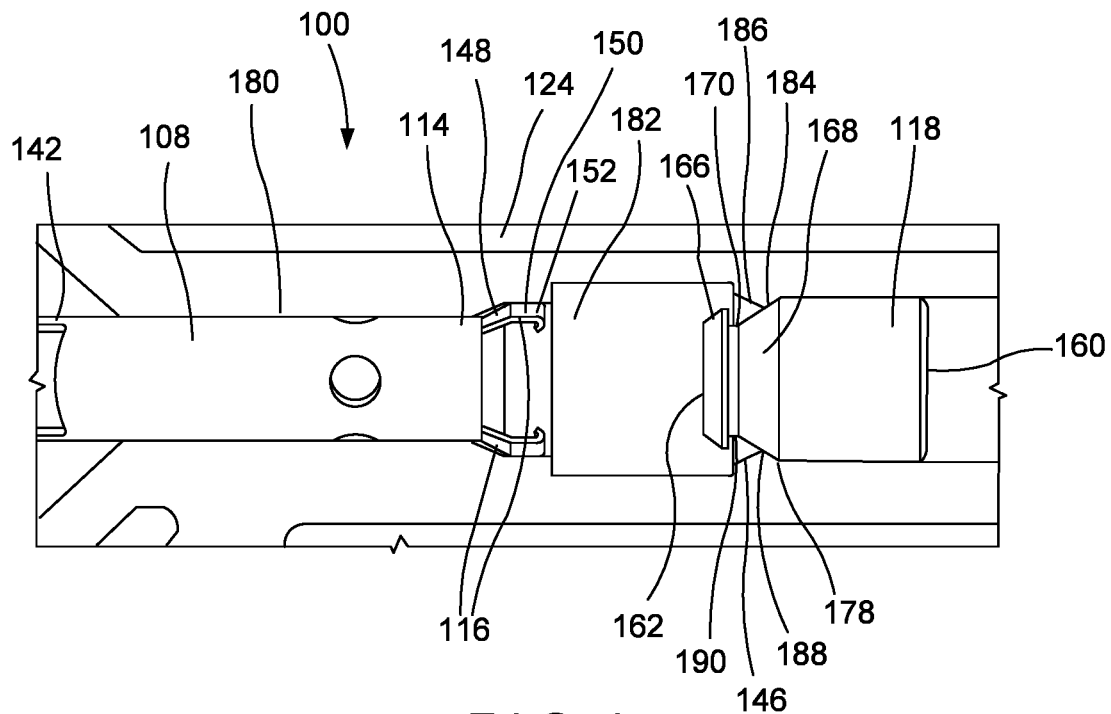
FIG. 4 shows a side view of a capsule and a bushing within the cartridge prior during a loading of the clip onto the applicator according to the system of FIG. 1.

In this embodiment, the longitudinal slot 182 includes a stop configured as a shoulder 184 sized to engage the proximal end 178 of the second ramped portion 168 so that the bushing 118 cannot be moved distally therebeyond, as shown in FIG. 4. The crimping feature 146 is positioned immediately distal of the shoulder 184 within the longitudinal slot 182. In this embodiment, the crimping feature 146 is configured as a ramped surface 186 flaring distally outward from the shoulder 184 so that the ramped surface 186 is angled with respect to the longitudinal axis of the capsule 108. A cross-sectional area (e.g., diameter) of the longitudinal slot 182 at a proximal end 188 of the ramped surface 186 is smaller than a cross-sectional area (e.g., diameter) at a distal end 190 of the ramped surface 186 so that the proximal end 188 protrudes into the longitudinal slot 182, toward a centerline thereof, to provide a crimping for the connecting elements 116.

Figure 5:
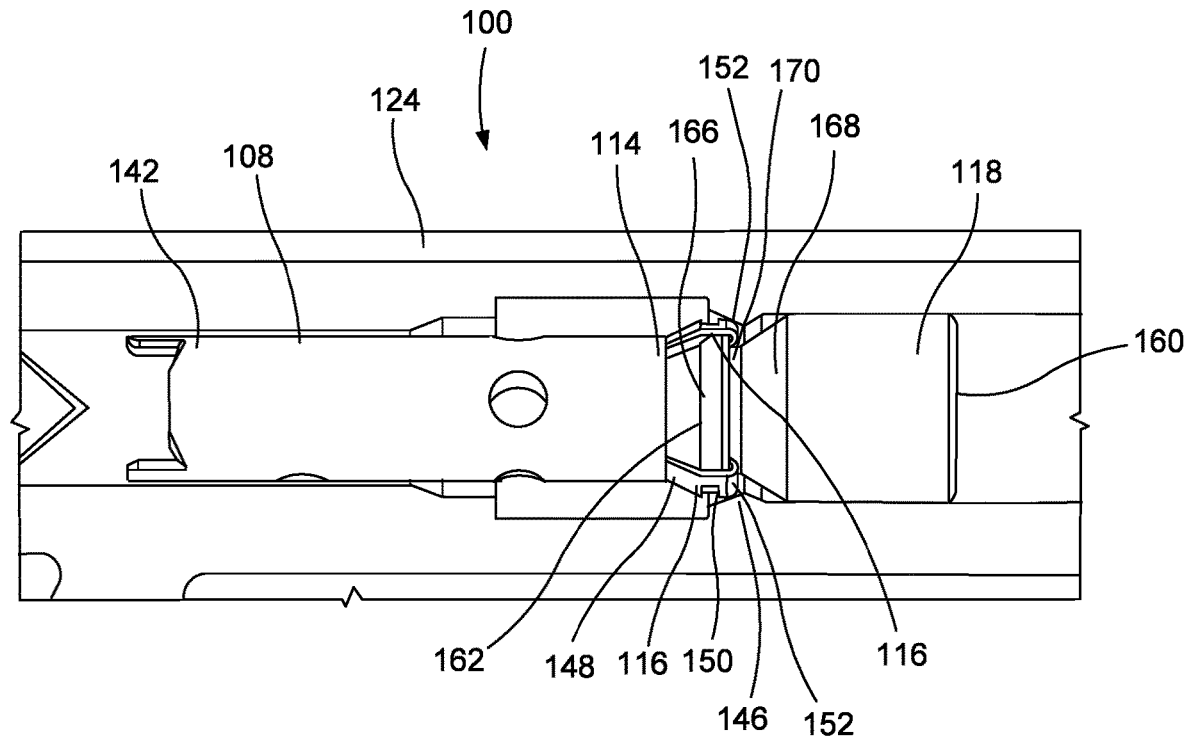
FIG. 5 shows a side view of the capsule drawn proximally over the bushing during loading of the clip according to the system of FIG. 1.

During loading of the clip 102 onto the applicator 104, a distal portion of the applicator 104, including the bushing 118, is inserted through the longitudinal slot 182 of the cartridge 124 until the proximal end 178 of the second ramped portion 168 abuts the shoulder 184, preventing the bushing 118 from moving therebeyond. In one embodiment, the control member 120 is then moved distally relative to the flexible member 156 until the enlarged distal end 122 of the control member 120 extends distally past the bushing 118 to engage the yoke 126. Upon connection of the control member 120 within the yoke 126, the control member 120 is drawn proximally relative to the flexible member 156 to move the clip 102 toward the closed configuration. Once in the closed configuration, continued proximal motion of the control member 120 moves the capsule 108 proximally relative to the cartridge 124 until the connecting elements 116 at the proximal end 114 of the capsule 108 are moved proximally over the first ramped portion 166, as shown in FIG. 5.

Figure 6:
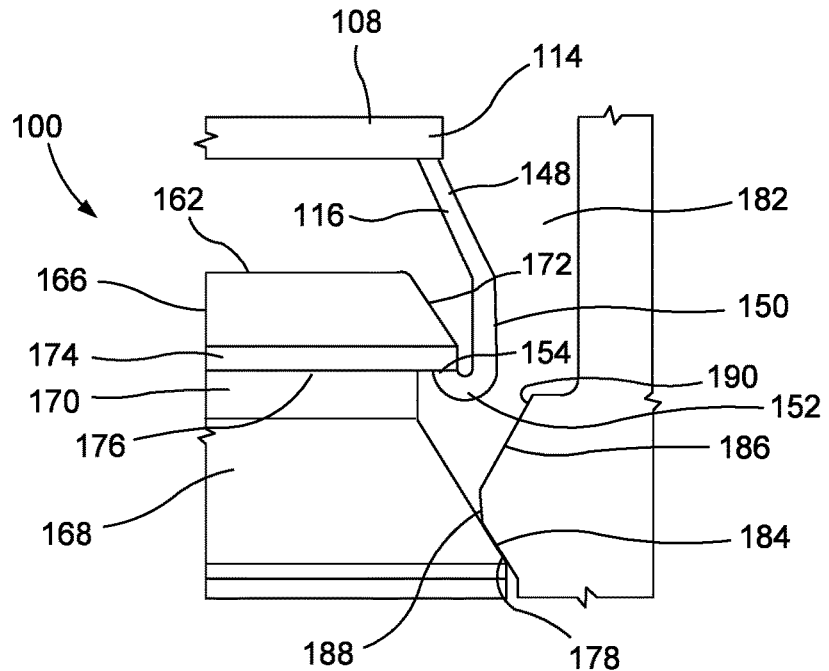
FIG. 6 shows an enlarged side view of a portion of the capsule and bushing preliminarily engaging one another during loading of the clip according to the system of FIG. 1.

In another embodiment, the shoulder 184 may be positioned in such a way that the user directly engages the connecting elements 116 onto the bushing 118, and then engages the control member 120 with the yoke 126 before finally removing the entire assembly from the cartridge 124 to fully crimp the clip onto the bushing 118. The hook 152 of each of the connecting elements 116 slides proximally along the exterior surface 172 of the first ramped portion 166, elastically deforming to accommodate the first ramped portion 166, until the hook 152 moves proximally past the lip 174 at which point, the connecting elements 116 revert to their initial configuration. In particular, the hook 152 is snapped over the first ramped portion 166, as shown in FIG. 6, forming the preliminary engagement with the hook 152 engaging the lip 174, as shown in FIG. 6, with the tip 154 of the hook 152 engaging the edge 176 of the lip 174.

Figure 7:
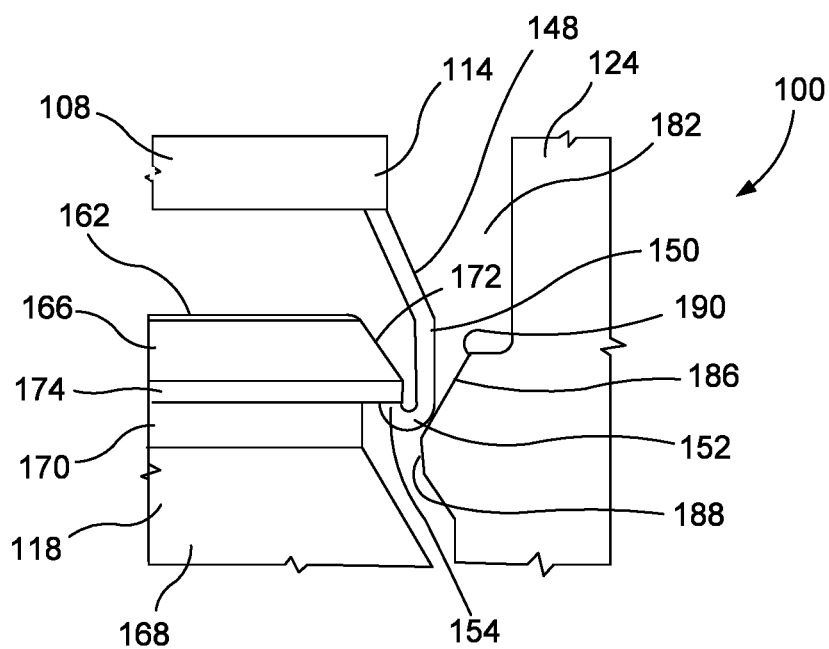
FIG. 7 shows an enlarged side view of a connecting element of the capsule engaging a crimping feature of the cartridge during loading of the clip according to the system of FIG. 1.
Figure 8:
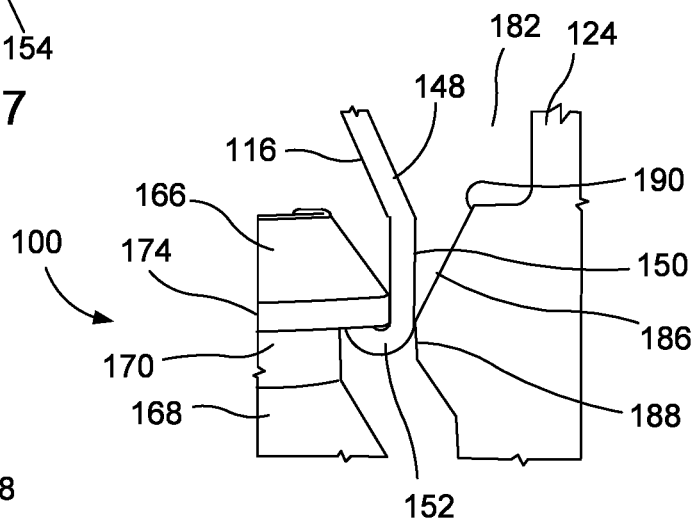
FIG. 8 shows an enlarged side view of the connecting element being crimped over a portion of the bushing during loading of the clip according to the system of FIG. 1.
Figure 9:
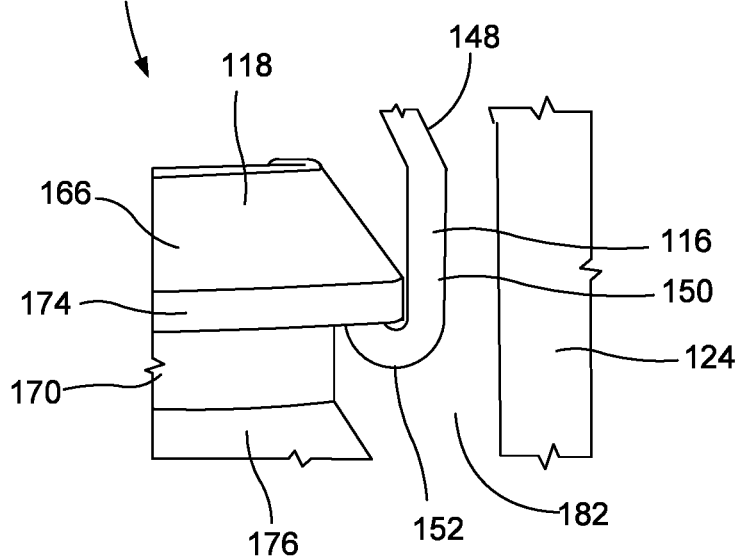
FIG. 9 shows the assembled clip and applicator being withdrawn from the cartridge according to the system of FIG. 1.

The snapping of the hook 152 over the first ramped portion 166 provides tactile feedback to the user so that the user is aware that the capsule 108 and the bushing 118 have formed a preliminary engagement. The user may then draw the entire applicator 104 proximally relative to the cartridge 124 so that the capsule 108, is also drawn proximally through the longitudinal slot 182 of the cartridge 124 until proximal portion 150 of the connecting elements 116 engage the crimping feature 146. In particular, the hook 152 of the distal portion is slid proximally along the ramped surface 186, as shown in FIG. 7, so that the crimping feature 146 provides both a radially inward and distal force to the hook 152, crimping the hook 152 over the lip 174 of the first ramped portion 166, as shown in FIG. 8.

For example, the tip 154 of the hook 152 may be received within the space defined between the exterior surface of the neck portion 170 and the interior surface of the ramped portion 166. A remaining portion of the proximal portion 150 of the connecting elements 116 is pressed against an exterior surface of the lip 174 forming a crimped connection which bears the load of the clip 102 opening and closing. Once the clip 102 has been loaded onto the applicator via the crimping of the connecting elements 116, further proximal motion of the applicator 104, as shown in 9, moves the bushing 118 and the capsule 108 proximally past the crimping feature 146 so that the assembled clip 102 and applicator 104 may be removed from the cartridge 124.

In use, after the clip 102 has been loaded onto the applicator 104, the clip 102, in the closed configuration, is inserted into the body to a location adjacent to target tissue via, for example, a working channel of an endoscope. Once the clip 102 has reached the target tissue, the clip 102 is moved toward the open configuration to receive the target tissue between the distal ends 112 of the clip arms 106. The clip 102 may be moved between the open and the closed configurations until the target tissue has been clipped between the clip arms 106, as desired. Once the clip 102 is in the closed configuration clipping the target tissue as desired, the control member 120 (e.g., via actuators of the handle portion 158) is moved proximally with respect to the capsule 108 until locking features of the clip arms 106 engage corresponding locking structures of the capsule 108, locking the clip arms 106 relative to the capsule 108 in the closed configuration.

To free the clip 102 from the applicator 104, the control member 120 is drawn further proximally until the capsule 108 is drawn proximally against the bushing 118 and a compressive load on the connecting elements 116 exceeds a predetermined threshold value, forcing the connecting elements 116, and in particular the hooks 152, to disengage from the lip 174 and slide proximally along the second ramped portion 168. The sliding of the hooks 152 along the second ramped portion 168 plastically deforms the connecting tabs 116 so that they remain in a more radially outward position further from the longitudinal axis of the capsule 108 out of engagement with the bushing 118. The bushing 118 may be proximally withdrawn from between the connecting elements 116, leaving the clip 102 in place clipping the target tissue.

The user continues to exert proximal force on the control member 120 until the yoke 126 breaks, fails or otherwise separates at the point 132, releasing the clip arms 106, and thereby the clip 102, from the control member 120 and locking the clip 102 closed over the target tissue. The entire applicator 104, including the control member 120 and the proximal portion 128 of the yoke 126, may then be withdrawn proximally from the body leaving the clip 102 clipped over the target tissue. If so desired, a new clip 102 may be loaded onto the applicator 104, in the same manner as described above, so that the system 100 may then be used to clip a second portion of tissue. This process may be repeated using the same applicator 104 as many times as needed or desired.

Although the connecting elements 116 are described and shown as extending proximally from the capsule 108 to engage a portion of the bushing 118, it will be understood by those of skill in the art that connecting elements 116 may similarly extend distally from a bushing of an applicator to engage a corresponding portion of a capsule of a clip. Alternatively, a coupler including crimpable connecting elements may be attached to either the capsule or the bushing to be crimped over a corresponding portion of the other of the capsule or the bushing.

It will be apparent to those skilled in the art that various modifications may be made in the present disclosure, without departing from the scope of the disclosure.

What is claimed is:

1. A method for loading a clip onto an applicator for a reloadable clipping system, comprising:
   inserting a distal portion of an applicator through a longitudinal slot of a cartridge in which a clip is stored, the longitudinal slot extending proximally of a space within the cartridge that is sized and shaped to house the clip in an open configuration;
   moving a control member of the applicator distally relative to the cartridge until an enlarged distal end of the control member is coupled to proximal ends of clip arms of the clip;
   moving a capsule of the clip proximally relative to the applicator via the control member so that connecting elements extending proximally from a proximal end of the capsule slide along an exterior surface of a first ramped portion of a bushing of the applicator until a hook at a proximal end of each of the connecting elements is moved distally beyond a proximal end of the first ramped portion, snapping thereover to form a preliminary engagement; and drawing the applicator proximally relative to the cartridge so that the hook of each of the connecting elements of the capsule, which is preliminarily engaged to the bushing, is moved proximally over a crimping feature along the longitudinal slot of the cartridge, the crimping feature engaging the hook to crimp the hook over a lip at the proximal end of the first ramped portion.

2. The method of claim 1, wherein the distal portion of the applicator is inserted through the longitudinal slot until a portion of the bushing engages a stop extending along a portion of the longitudinal slot.

3. The method of claim 1, wherein the crimping feature is configured as a ramped surface angled so that when the connecting elements are moved proximally therealong, the ramped surface exerts both a distal and radially inward force on the hook to crimp the hook over the lip.

4. The method of claim 3, wherein the lip is defined via a cavity extending between an interior surface of the first ramped portion and an exterior surface of a neck portion extending proximally from the first ramped portion, a tip of the hook received within the cavity when the hook is crimped over the lip.

5. The method of claim 4, wherein the bushing of the applicator includes a second ramped portion flaring proximally outward from a proximal end of the neck portion.

6. The method of claim 5, wherein the first and second ramped portions define substantially conically shaped portions of the bushing while the neck portion extends along a cylindrical portion of the bushing.

7. The method of claim 1, further comprising:
drawing the applicator further proximally relative to the cartridge to draw the clip out of the cartridge.

8. The method of claim 1, wherein the hook extends along a substantially J-shape so that a tip of the hook extends toward a distal direction.

9. The method of claim 1, wherein the connecting elements are formed of a metal material configured to permit elastic deformation thereof during coupling of the capsule to the applicator and to permit plastic deformation without fracture thereof when the clip is deployed from the applicator.

10. The method of claim 1, wherein the clip arms are configured to be moved from the open configuration, in which distal ends of the clip arms are separated from one another, to a closed configuration, in which the distal ends of the clip arms are drawn toward one another.

11. The method of claim 10, wherein the clip arms are configured to be moved between the open configuration and the closed configuration via longitudinal movement of the control member relative to the capsule.

12. The method of claim 10, wherein the clip arms are biased toward the open configuration.

13. The method of claim 10, wherein the clip arms are in the closed configuration when the clip is drawn out of the cartridge by moving the applicator proximally relative to the cartridge.

* * * * *